United States Patent

Torii et al.

[11] Patent Number: 5,599,925
[45] Date of Patent: Feb. 4, 1997

[54] PENAM DERIVATIVES

[75] Inventors: Shigeru Torii, Okayama-ken; Hideo Tanaka, Okayama; Masatoshi Taniguchi, Toyonaka; Mitio Sasaoka; Takashi Shiroi, both of Tokushima-ken; Yutaka Kameyama, Okayama, all of Japan

[73] Assignee: Otsuka Kagaku Kabushiki Kaisha, Osaka, Japan

[21] Appl. No.: 314,307

[22] Filed: Sep. 30, 1994

Related U.S. Application Data

[63] Continuation of Ser. No. 849,707, Mar. 11, 1992, abandoned.

[30] Foreign Application Priority Data

Mar. 13, 1991 [JP] Japan ................................. 3-047085
Mar. 13, 1991 [JP] Japan ................................. 3-047166

[51] Int. Cl.$^6$ .................................................. C07D 499/897
[52] U.S. Cl. ............................................ 540/310; 540/313
[58] Field of Search .................................. 514/192, 210; 540/310, 313

[56] References Cited

U.S. PATENT DOCUMENTS

| | | | |
|---|---|---|---|
| 4,331,677 | 5/1982 | Foyler et al. | 540/310 |
| 4,797,396 | 1/1989 | Finke et al. | 514/210 |
| 4,861,768 | 8/1989 | Torii et al. | 540/310 |
| 4,912,213 | 3/1990 | Taniguchi et al. | 540/310 |
| 5,089,489 | 2/1992 | Alpegiani et al. | 540/310 |

*Primary Examiner*—John M. Ford
*Attorney, Agent, or Firm*—Armstrong, Westerman, Hattori, McLeland & Naughton

[57] ABSTRACT

A penam derivative of the general formula

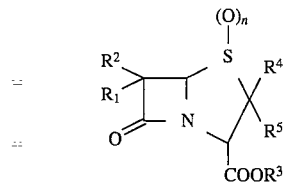

wherein $R^1$ means hydrogen, halogen, amino or protected amino; $R^2$ means hydrogen, halogen, lower alkoxy, lower acyl, lower alkyl, hydroxy- or protected hydroxy-substituted lower alkyl, hydroxy or protected hydroxy, or $R^1$ and $R^2$ may jointly represent oxo; $R^3$ means hydrogen or a carboxy-protecting group; $R^4$ means hydrogen; $R^5$ means a group of the formula $-CH_2Y$ where Y means halogen, $-N_3$, $-ONO_2$, $-OR^6$, $-OCOR^6$, $-SCSOR^6$, $-SCSN(R^6)_2$, $-SR^6$, $-SO_2R^6$, $-NHR^6$, $-N(R^6)_2$ or a substituted or unsubstituted nitrogen-containing heterocyclic group having a free valence on nitrogen; $R^6$ means a lower alkyl, aryl or heterocyclic group which is substituted or unsubstituted; or $R^4$ and $R^5$ may jointly represent $=CH_2$; n means 0, 1 or 2; provided, however, that where $R^4$ and $R^5$ jointly represent $=CH_2$, n is not equal to 0.

3 Claims, No Drawings

PENAM DERIVATIVES

This application is a continuation of application Ser. No. 07/849,707 filed Mar. 11, 1992, now abandoned.

The present invention relates to novel penam derivatives and processes for producing the same.

The penam derivatives of the invention are novel compounds, never described in literature before, and have the following general formula.

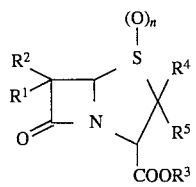

(1)

wherein $R^1$ means hydrogen, halogen, amino or protected amino; $R^2$ means hydrogen, halogen, lower alkoxy, lower acyl, lower alkyl, hydroxy- or protected hydroxy-substituted lower alkyl, hydroxy or protected hydroxy, or $R^1$ and $R^2$ may jointly represent oxo; $R^3$ means hydrogen or a carboxy-protecting group; $R^4$ means hydrogen; $R^5$ means a group of the formula $-CH_2Y$ where Y means halogen, $-N_3$, $-ONO_2$, $-OR^6$, $-OCOR^6$, $-SCSOR^6$, $-SCSN(R^6)_2$, $-SR^6$—$SO_2 R^6NHR^6$, $-N(R^6)_2$ or a substituted or unsubstituted nitrogen-containing heterocyclic group having a free valence on nitrogen; $R^6$ means a lower alkyl, aryl or heterocyclic group which is substituted or unsubstituted; or $R^4$ and $R^5$ may jointly represent $=CH_2$; n means 0, 1 or 2; provided, however, that where $R^4$ and $R^5$ jointly represent $=CH_2$, n is not equal to 0.

The penam derivatives of the above general formula (1) can be roughly classified into two groups, viz. penam derivatives of general formula (1a) and 2-exo-methylenepenam oxide derivatives of general formula (1b), as shown below.

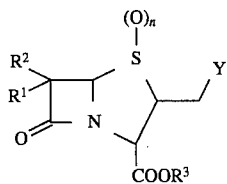

(1a)

wherein $R^1$, $R^2$, $R^3$, Y and n are as defined above

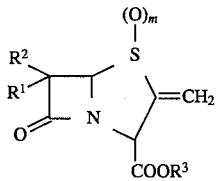

(1b)

wherein $R^1$, $R^2$, $R^3$ and Y are as defined above; m is equal to 1 or 2.

It is an object of the invention to provide a broad-spectrum penam derivative (1a) which is highly active against both gram-positive and gram-negative bacteria, stable against various β-lactamases and active even against resistant strains.

It is another object of the invention to provide an 2-exomethylenepenam oxide derivative (1b) which can be used with advantage as a synthetic intermediate in the production of said penam derivative (1a).

It is still another object of the invention to provide processes for producing said penam derivative (1a) and 2-exomethylenepenam oxide derivative (1b).

Other features and advantages of the present invention will become apparent as the following detailed description proceeds.

The atomic groups relevant to the invention are defined below.

The 'halogen' may for example be fluorine, chlorine, bromine or iodine.

The 'lower alkyl' means a $C_{1-4}$ straight-chain or branched alkyl group such as methyl, ethyl, n-propyl, isopropyl, n-butyl, isobutyl, sec-butyl, tert-butyl and so on.

The 'aryl' means phenyl or naphthyl, for instance.

The 'protected amino' $R^1$ includes the various groups mentioned in Theodora W. Greene: Protective Groups in Organic Synthesis, Chapter 7, pp. 218–287 as well as phenoxyacetamido, p-methylphenoxyacetamido, p-methoxy-phenoxyacetamido, p-chlorophenoxyacetamido, p-bromo-phenoxyacetamido, phenylacetamido, p-methylphenyl-acetamido, p-methoxyphenylacetamido, p-chlorophenylace-tamido, p-bromophenylacetamido, phenylmonochloroacetamido, phenyldichloroacetamido, phenylhydroxyacetamido, thienylacetamido, phenylacetoxyacetamido, α-oxophenyl-acetamido, benzamido, p-methylbenzamido, p-methoxy-benzamido, p-chlorobenzamido, p-bromobenzamido, phenyl-glycylamido, amino-protected phenylglycylamido, p-hydroxyphenylglycylamido, either amino- or hydroxy-protected or amino- and hydroxy-protected p-hydroxyphenylglycylamido and so on. The protective group for the amino group of said phenylglycylamido or p-hydroxy-phenylglycylamido includes the various groups mentioned in the above literature, Chapter 7, pp. 218–287. The protective group for the hydroxyl group of p-hydroxyphenylglycylamido includes the various groups mentioned in the same literature, Chapter 2, pp. 10–72. The protected amino $R^1$ may be one of the acyl groups which are commonly employed in the field of penicillins and cephalosporins. The acyl group derived from a carboxylic acid, for instance, includes, among others, formyl, acetyl, 2,6-dimethoxyphenylcarbonyl, 5-methyl-3-phenylisoxazol-4-ylcarbonyl, 4-aminomethylphenylacetyl, hydroxyacetyl, phenoxyacetyl, 1-tetrazolylacetyl, cyanomethylthioacetyl, carboxyethylthioacetyl, 2-thienylacetyl, α-bromo-2-thienylacetyl, 5-methoxy-2thienylacetyl, phenylacetyl, α-aminophenylacetyl, α-hydroxyphenylacetyl, α-carboxyphenylacetyl, α-sulfophenylacetyl, 3-bromophenylacetyl, α-(4-ethyl-2,3-dioxo-1-piperazinecarboxamido)-α-phenylacetyl, α-(4-ethyl-2,3-dioxo-1-piperazinecarboxamido)-α-(p-hydroxyphenyl)acetyl, α-(4-ethyl-2,3-dioxo-1-piperazinecarboxamido)-α-(3,4-dihydroxyphenyl)acetyl, α-(4-ethyl-2,3-dioxo-1-piperazinecarboxamido)-α-(3,4-diacetoxyphenyl) acetyl, α-(4-ethyl-2,3-dioxo-1-piperazinecarboxamido)-α-(3,4-diacetoxy-6-chlorophenyl)acetyl, α-(4-ethyl-2,3-dioxo-1-piperazinecarboxamido)-α-(3,4-diacetoxy-6-fluorophenyl)acetyl, α-(4-ethyl-2,3-dioxo-1-piperazinecarboxamido)-α-(2-aminothiazol-4-yl)acetyl, α-(4-ethyl-2,3-dioxo-1-piperazinecarboxamido)-α-(6-chloro-3,4-dihydroxyphenyl)acetyl, α-(4-ethyl-2,3-dioxo-1-piperazinecarboxamido)-α-(6-fluoro-3,4-dihydroxyphenyl)acetyl, α-(4-ethyl-2,3-dioxo-1-piperazinecarboxamido)benzothienylacetyl, α-(4-cyclopropyl-2,3-dioxo-1-piperazinecarboxamido)-α-phenyl acetyl, α-(2-oxo-1-imidazolidinecarboxamido)-α-phenylacetyl, α-[3-(methylsulfonyl)-2-oxo-1-imidazolidine-carboxamido]-α-phenylacetyl, α-(4-hydroxy-1,5-naphthylidine-3-carboxamido)-α-phenylacetyl, α-(4-phenyl-2,3-dioxo-1-piperazinecarboxamido)-phenylacetyl, α-[4-(2,4-dichlorophenyl)-2,3-dioxo-1-piperazinecarboxamido]-α-phenylacetyl, α-(4-oxo-4H-thiopyran-3-ylcarboxamido)-α- phenylacetyl, 2-thienyl-2-methoxyiminoacetyl, 2-(2-aminothoazol-4-yl)acetyl, 2-(2-aminothiazol-4-yl)-2-methoxyiminoacetyl, α-difluoromethylthioacetyl, α-(cis-2-cyanovinyl)thioacetyl, α-[3-(4-phenylphenylcarbonyl)-3-methyl-1-ureido]-α-phenylacetyl, α-{[4-(4-chlorophenylimidazol)-2-yl]carboxamido}-α-phenylacetyl, isobutyryl, 2-(5-amino-1,2,4-thiadiazol-3-yl)-2methoxyiminoacetyl, α-{1,2-dihydro-2-oxo-6-[2-(2pyridyl) ethenyl]-3-pyridylcarboxamido}-α-(4-hydroxyphenyl) acetyl, α-(5-hydroxy-4-pyridone-2-carbonylamino)-α-(2-aminothiazol-4-yl)acetyl, 2-(6,7-dihydroxychromone-3-carbixamido)-2-(4-hydroxyphenyl)acetyl, 2-(4-hydroxy-6-methylpyridin-3-yl)carboxamido-2-(4-hydroxyphenyl)acetyl, 2-{3-[2-(4-sulfamoylphenyl)amino-4-hydroxy-5-pyrimidinyl]}ureido-2-(4-hydroxyphenyl)acetyl and so on.

The 'lower alkoxy' $R^2$ means a $C_{1-4}$ straight-chain or branched alkoxy group such as methoxy, ethoxy, n-propoxy, isopropoxy, n-butoxy, isobutoxy, sec-butoxy, tert-butoxy and so on.

The 'lower acyl' $R^2$ means a $C_{1-4}$ straight-chain or branched acyl group such as formyl, acetyl, propionyl, butyryl, isobutyryl and so on.

The protected hydroxyl group of the 'hydroxy- or protected hydroxy-substituted lower alkyl' $R^2$ and the protective group of the protected hydroxyl group in $R^2$ may for example be the groups respectively mentioned in the above literature, Chapter 2, pp. 10–72. The 'substituted lower alkyl' $R^2$ may be substituted by hydroxy or/and any of substituents selected from among various species of protected hydroxy referred to above in one or more carbon positions.

The carboxy-protecting group $R^3$ includes not only the various groups mentioned in the above literature, Chapter 5, pp. 152–192 but also such other groups as benzyl, p-methoxybenzyl, p-nitrobenzyl, diphenylmethyl, trichloroethyl, tert-butyl and so on.

The nitrogen-containing heterocyclic group Y having a free valence on nitrogen includes, among others, piperidino, morpholino, 1-piperazinyl, 1-pyrrolidinyl, 1-imidazolidinyl, 1-pyrazolidinyl, 2-pyrrolin-1-yl, 2-imidazolin-1-yl, 3-pyrazolin-1-yl, 1-indolinyl, 2isoindolinyl, 1-pyrrolyl, 2-isoindolyl, 1-imidazolyl, 1-pyrazolyl, 1-benzimidazolyl, 1H-1-indazolyl, 1-triazolyl, 1-tetrazolyl, phthaloyl and so on.

The heterocyclic moiety of said optionally substituted heterocyclic group $R^6$ includes 4-, 5- and 6-membered or fused heterocyclic groups containing at least one heteroatom selected from among oxygen, nitrogen and sulfur, such as thienyl, furyl, pyrrolyl, oxazolyl, benzoxazolyl, isoxazolyl, thiazolyl, benzothiazolyl, isothiazolyl, imidazolyl, benzimidazolyl, 1,2,3-thiadiazolyl, 1,3,4-thiadiazolyl, 1,2,4-thiadiazolyl, 1,3,4-oxadiazolyl, 1,2,3-triazolyl, 1,2,4-triazolyl, tetrazolyl, pyridyl, quinolyl, isoquinolyl, pyrimidinyl, pyrazinyl, pyridazinyl, 1,2,3,4-tetrahydroquinolyl, 1,2,4-triazinyl, imidazo[1,2-b][1,2,4]triazinyl, pyrrolidinyl, morpholinyl, quinuclidinyl, 2,3,4-tritetrahydroquinolyl and so on. The nitrogen-containing heterocyclic groups may be quaternized.

The substituent group which may be present on said substituted nitrogen-containing heterocyclic group Y or on said substituted lower alkyl, substituted aryl or substituted heterocyclic group $R^6$ includes, among others, halogen, hydroxy, nitro, cyano, aryl, lower alkyl, amino, mono-lower alkylamino, di-lower alkylamino, mercapto, alkyl- or arylthio of the formula $R^7S$— ($R^7$ means lower alkyl or aryl), formyloxy, acyloxy of the formula $R^7COO$—($R^7$ is as defined above), formyl, acyl of the formula $R^7CO$—($R^7$ is as defined above), alkoxy or aryloxy of the formula $R^7O$—($R^7$ is as defined above), carboxy, alkoxy- or aryloxycarbonyl of the formula $R^7OCO$—($R^7$ is as defined above) and so on. The nitrogen-containing heterocyclic group Y and the lower alkyl, aryl or heterocyclic group $R^6$ may be substituted by one or more substituent groups like those mentioned hereinbefore, which substituent groups may be the same or different.

The 2-exomethylenepenam oxide derivative of general formula (1b) can be produced by the following and other processes. Thus, the derivative (1b) can be easily produced by oxidizing an 2-exomethylenepenam derivative of the following general formula with an oxidizing agent.

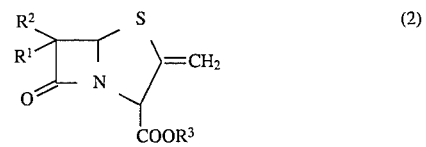

wherein $R^1$, $R^2$ and $R^3$ are as defined hereinbefore.

This reaction is carried out in an appropriate solvent. The solvent mentioned just above includes, among others, alcohols such as methanol, ethanol, propanol, isopropyl alcohol, butanol, tert-butanol, etc.; lower alkyl esters of lower carboxylic acids, such as methyl formate, ethyl formate, propyl formate, butyl formate, methyl acetate, ethyl acetate, propyl acetate, butyl acetate, methyl propionate, ethyl propionate, etc.; ketones such as acetone, methyl ethyl ketone, methyl propyl ketone, methyl butyl ketone, methyl isobutyl ketone, diethyl ketone, etc.; ethers such as diethyl ether, ethyl propyl ether, ethyl butyl ether, dipropyl ether, diisopropyl ether, dibutyl ether, methylcellosolve, dimethoxyethane, etc.; cyclic ethers such as tetrahydrofuran, dioxane, etc.; nitriles such as acetonitrile, propionitrile, butyronitrile, isobutyronitrile, valeronitrile, etc.; substituted or unsubstituted aromatic hydrocarbons such as benzene, toluene, xylene, chlorobenzene, anisole, etc.; halogenated hydrocarbons such as dichloromethane, chloroform, dichloroethane, trichloroethane, dibromoethane, propylene dichloride, carbon tetrachloride, freons, etc.; aliphatic hydrocarbons such as pentane, hexane, heptane, octane, etc.; cycloalkanes such as cyclopentane, cyclohexane, cycloheptane, cyclooctane, etc. and amides such as dimethylformamide, dimethylacetamide, etc.; and dimethyl sulfoxide. These solvents can be used alone or in combination. Where necessary, these organic solvents may contain water. The solvent is used in an amount of about 10 to about 200 l, preferably about 20 to about 100 l, per kg of compound (2).

The oxidizing agent for this reaction may be selected from a broad range of oxidizing agents which are used in the oxidation of sulfides. To be specific, inorganic oxides such as manganese dioxide, chromic acid, lead tetracetate, ruthenium tetroxide, potassium permanganate, etc.; periodic acid compounds such as periodic acid, sodium periodate, etc.; N-halocarboxamides such as N-bromosuccinimide, N-chlorosuccinimide, etc.; organic peracids such as t-butyl hypochlorite, hydrogen peroxide, performic acid, peracetic acid, m-chloroperbenzoic acid, etc.; and combinations of hydrogen peroxide with lower carboxylic acids such as formic acid, acetic acid, etc. may be mentioned by way of example. The proper proportion of such oxidizing agent varies with different substrate compounds and whether n in the contemplated object compound is equal to 1 or 2. Generally speaking, the oxidizing agent is used in an amount of about 1 to about 20 mols, preferably about 1 to 5 mols, per mol of compound (2).

The preferred reaction temperature is generally about −50° C. to about 80° C., preferably about −10° C. to about 50° C.

The resulting compound of the invention can be isolated and purified by the conventional procedures such as filtration, recrystallization, column chromatography, preparative thin-layer chromatography and so on.

The penam derivative of general formula (1a) wherein n is equal to 1 or 2 can be easily produced by reacting an 2-exomethylenepenam oxide derivative of general formula (1b), which is obtainable as above, with a nucleophilic reagent of the general formula:

Y–H     (3)

wherein Y is as defined hereinbefore.

This reaction is conducted in an appropriate solvent. The solvent mentioned just above can be selected from among, for example, alcohols such as methanol, ethanol, propanol, isopropyl alcohol, butanol, tert-butanol, etc.; lower alkyl esters of lower carboxylic acids, such as methyl formate, ethyl formate, propyl formate, butyl formate, methyl acetate, ethyl acetate, propyl acetate, butyl acetate, methyl propionate, ethyl propionate, etc.; ketones such as acetone, methyl ethyl ketone, methyl propyl ketone, methyl butyl ketone, methyl isobutyl ketone, diethyl ketone, etc.; ethers such as diethyl ether, ethyl propyl ether, ethyl butyl ether, dipropyl ether, diisopropyl ether, dibutyl ether, methylcellosolve, dimethoxyethane, etc.; cyclic ethers such as tetrahydrofuran, dioxane, etc.; nitriles such as acetonitrile, propionitrile, butyronitrile, isobutyronitrile, valeronitrile, etc.; substituted or unsubstituted aromatic hydrocarbons such as benzene, toluene, xylene, chlorobenzene, anisole, etc.; halogenated hydrocarbons such as dichloromethane, chloroform, dichloroethane, trichloroethane, dibromoethane, propylene dichloride, carbon tetrachloride, freons, etc., aliphatic hydrocarbons such as pentane, hexane, heptane, octane, etc.; cycloalkanes such as cyclopentane, cyclohexane, cycloheptane, cyclooctane, etc.; amides such as dimethylformamide, dimethylacetamide, etc.; and dimethyl sulfoxide. These solvents can be used alone or in combination. Where necessary, these organic solvents may contain water. The solvent is used in an amount of about 10 to about 200 l, about 20 to about 100 l, per kg of compound (1b).

The reaction may be conducted in the presence of a base. The base includes, among others, hydroxides of alkali metals, such as sodium hydroxide, potassium hydroxide, etc.; hydroxides of alkaline earth metals, such as calcium hydroxide, barium hydroxide, etc.; carbonates of alkali metals, such as potassium carbonate, sodium carbonate, etc.; hydrides of alkali metals, such as lithium hydride, potassium hydride, sodium hydride, etc.; and alkyl- or aryllithium such as methyllithium, n-butyllithium, phenyllithium and so on. The base is used in an amount of about 0.001 to about 10 mols, preferably about 0.01 to about 1 mols, per mol of compound (1b).

The amount of the nucleophilic reagent of general formula (3) is generally about 1 to about 50 mols, preferably 1 to 10 mols, per mol of compound (1b). It may be so arranged that prior to the above reaction the nucleophilic reagent (3) is reacted with the base to prepare a compound of the general formula

Y–M     (4)

wherein M means an alkali metal or alkaline earth metal.

The above reaction is conducted generally at about –78° C. to about 100° C., preferably at about –78° 50 C.

The resulting penam derivative of general formula (1a) wherein n is equal to 1 or 2 can be isolated and purified by the conventional procedures such as filtration, recrystallization, column chromatography, pre parative thin-layer chromatography and so on.

The penam derivative of general formula (1a) wherein n is equal to 1 or 2 can be subjected to reduction in the manner well known to chemists in this field, namely any of the processes described in J. Chem. Soc., Perkin. Trans. 1, 932 (1973), Tetrahedron Lett. 13, 971 (1976), the specification of Japanese Patent Publication No. 56-24675, etc. or any process analogous thereto, to give the corresponding penam derivative of general formula (1a) wherein n is equal to 0.

The resulting penam derivative of general formula (1a) wherein n is equal to 0 can be isolated and purified by the conventional procedures such as filtration, recrystallization, column chromatography, preparative thin-layer chromatograhy and so on.

The compound (2) which is used as the starting compound in the present invention can be easily produced, for example by reacting an allenyl β-lactam compound of the following general formula with a metallic reducing agent.

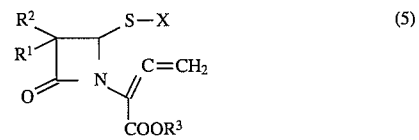

(5)

wherein $R^1$, $R^2$ and $R^3$ are as defined hereinbefore; X means —$SO_2R^6$ or —$SR^6$, where $R^6$ is as defined hereinbefore.

The reaction for conversion of compound (5) to compound (2) is carried out in an organic solvent. The organic solvent mentioned just above can be selected from a broad range of known solvents which are capable of dissolving compound (5) and inert to the reaction. Included among such solvents are alcohols such as methanol, ethanol, propanol, isopropyl alcohol, butanol, tert-butanol, etc.; lower alkyl esters of lower carboxylic acids, such as methyl formate, ethyl formate, propyl formate, butyl formate, methyl acetate, ethyl acetate, propyl acetate, butyl acetate, methyl propionate, ethyl propionate, etc.; ketones such as acetone, methyl ethyl ketone, methyl propyl ketone, methyl butyl ketone, methyl isobutyl ketone, diethyl ketone, etc.; ethers such as diethyl ether, ethyl propyl ether, ethyl butyl ether, dipropyl ether, diisopropyl ether, dibutyl ether, methylcellosolve, dimethoxyethane, etc.; cyclic ethers such as tetrahydrofuran, dioxane, etc.; nitriles such as acetonitrile, propionitrile, butyronitrile, isobutyronitrile, valeronitrile, etc.; substituted or unsubstituted aromatic hydrocarbons such as benzene, toluene, xylene, chlorobenzene, anisole, etc.; halogenated hydrocarbons such as dichloromethane, chloroform, dichloroethane, trichloroethane, dibromoethane, propylene dichloride, carbon tetrachloride, freons, etc.; aliphatic hydrocarbons such as pentane, hexane, heptane, octane, etc.; cycloalkanes such as cyclopentane, cyclohexane, cycloheptane, cyclooctane, etc. and amides such as dimethylformamide, dimethylacetamide, etc.; and dimethyl sulfoxide. These solvents can be used alone or in combination. The organic solvent is used in an amount of about 0.5 to about 200 l, preferably about 10 l, per kg of compound (5).

The metallic reducing agent for the above reaction can be selected from among, for example, lead metal, titanium metal, zirconium metal, gallium metal, bismuth metal, antimony metal and so on. The morphology of such metal is not critical. Thus, it can be a dust, plate, block or wire, for instance. In order to carry the reaction to completion at a relatively low temperature in a short time period, the metal is preferably in the dust form. The particle size of the dust can be selected from a broad range but is preferably about 10 to about 500 meshes. The proportion of such metallic reducing agent is generally about 1 to 10 mols, preferably about 1 to 4 mols, per mol of compound (5).

The above reaction is preferably conducted in the presence of another metal having a greater ionization tendency than said metallic reducing agent. In the presence of such a metal, the amount of said metallic reducing agent can be drastically decreased the workup procedure following the reaction be facilitated, and the reaction itself be conducted at a lower temperature in a reduced time. Specific examples of such combination of a metallic reducing agent and a metal having a greater ionization tendency are Pb/Al, Bi/Al, Ti/Zn, Ga/Zn, Zr/Zn, Sb/Zn, Te/Zn, Pb/Zn, Bi/Zn, Bi/Mg, Bi/Sn, Sb/Sn and so on. The morphology of the metal to be thus used in combination with said metallic reducing agent is also virtually unrestricted and can be selected from among a diversity of forms such as dust, plate, foil, block, wire and so on. In order that the reaction may be carried to completion at a lower temperature in a reduced time, the metal is preferably in the dust form. The particle size of such metal can be selected from a broad range but is preferably about 10 to 300 meshes. The proportion of the metal is generally about 1 to about 50 mols, preferably about 1 to about 10 mols, per mol of compound (5).

Where the above reaction is carried out in the presence of a metal having a greater ionization tendency than said metallic reducing agent, it is more desirable to employ a compound of such metal in lieu of said metallic reducing agent. Such metal compound includes, among others, lead halides such as lead fluoride, lead chloride, lead bromide, lead iodide, etc.; lead salts of inorganic acids, such as lead nitrate, lead sulfate, lead perchlorate, lead borate, lead carbonate, lead phosphate, etc.; lead salts of fatty acids, such as lead acetate, lead oxalate, lead stearate, etc.; lead oxide; lead hydroxide; titanium halides such as titanium fluoride, titanium chloride, titanium bromide, titanium iodide, etc.; titanium salts of inorganic acids, such as titanium sulfate, titanium nitrate, etc.; gallium halides such as gallium fluoride, gallium chloride, gallium bromide, gallium iodide, etc.; gallium salts of inorganic acids, such as gallium sulfate, gallium nitrate, gallium perchlorate, etc.; zirconium halides such as zirconium fluoride, zirconium chloride, zirconium bromide, zirconium iodide, etc.; zirconium sulfate; tellurium halides such as tellurium chloride, tellurium bromide, tellurium iodide, etc.; bismuth halides such as bismuth fluoride, bismuth chloride, bismuth bromide, bismuth iodide, etc.; bismuth salts of inorganic acids, such as bismuth nitrate, bismuth sulfate, etc.; bismuth oxide; antimony halides such as antimony fluoride, antimony chloride, antimony bromide, antimony iodide, etc.; antimony salts of inorganic acids, such as antimony sulfate, etc.; and antimony oxide. The proportion of such metal compound should theoretically be one molecule but, for practical purposes, it is used generally in a proportion of about 0.0001 to about 2 mols, per mol of compound (5).

The reaction temperature is dependent on the species of starting compound and organic solvent, among other factors, and cannot be stated in general terms. However, the reaction is carried out generally at about −20° C. to about 100° C., preferably at about 0° to about 50° C.

There are cases in which the reaction may be hastened by conducting it under ultra sonication.

After completion of the reaction, the reaction mixture can be subjected, for example, to a conventional extraction procedure to isolate the desired 2-exomethylenepenam derivative (2) in a substantially pure form. Where necessary, the product can be further purified by well-known purification procedures such as recrystallization, column chromatography and so on.

The above compound of general formula (5) can be produced, for example by reacting an azetidinone derivative of the following general formula with a base.

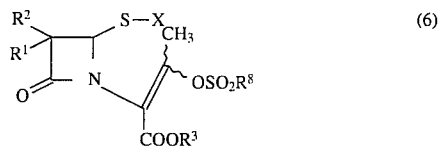

wherein $R^1$, $R^2$, $R^3$ and X are as defined hereinbefore; $R^8$ means a lower alkyl group which may optionally be substituted or an aryl group which may optionally be substituted.

The base for use in this reaction is preferably an aliphatic or aromatic amine, such as triethylamine, diisopropylamine, ethyldiisopropylamine, tributylamine, 1,5-diazabicyclo[3.4.0]nonene-5 (DBN), 1,8-diazabicyclo[5.4.0]undecene-7 (DBU), 1,4-diazabicyclo[2.2.0]-octane (DABCO), piperidine, N-methylpiperidine, 2,2,6,6-tetramethylpiperidine, morpholine, N-methylmorpholine, N,N-dimethylaniline, N,N-dimethylaminopyridine and so on. The proportion of the base is generally 1 to 12 mols, preferably 1 to 6 mols, per mol of compound (6). The solvent can be selected from a broad range of solvents which are capable of dissolving compound (6) and inert to the reaction. Thus, the solvent includes, among others, lower alkyl esters of lower carboxylic acids, such as methyl formate, ethyl formate, propyl formate, butyl formate, methyl acetate, ethyl acetate, propyl acetate, butyl acetate, methyl propionate, ethyl propionate, etc.; ethers such as diethyl ether, ethyl propyl ether, ethyl butyl ether, dipropyl ether, diisopropyl ether, dibutyl ether, methylcellosolve, dimethoxyethane, etc.; cyclic ethers such as tetrahydrofuran, dioxane, etc.; nitriles such as acetonitrile, propionitrile, butyronitrile, isobutyronitrile, valeronitrile, etc.; substituted or unsubstituted aromatic hydrocarbons such as benzene, toluene, xylene, chlorobenzene, anisole, etc.; halogenated hydrocarbons such as dichloromethane, chloroform, dichloroethane, trichloroethane, dibromoethane, propylene dichloride, carbon tetrachloride, freons, etc.; aliphatic hydrocarbons such as pentane, hexane, heptane, octane, etc.; cycloalkanes such as cyclopentane, cyclohexane, cycloheptane, cyclooctane, etc.; amides such as dimethylformamide, dimethylacetamide, etc.; dimethyl sulfoxide; and so on. These solvents may be used alone or in combination. Where necessary, these solvents may contain water. The solvent is used in an amount of about 0.5 to about 200 l, about 1 to about 50 l, per kg of compound (6). This reaction is carried out at a temperature between −70° C. and 100° C., preferably between −50° C. and 50° C. After completion of the reaction, the compound of general formula (5) can be isolated as a substantially pure substance by the conventional extraction or crystallization procedure. Of course, any other appropriate purification procedure may likewise be employed.

The compound of general formula (6) can be produced, *inter alia*, by the process described in Japanese Unexamined Patent Application No. 61-165367.

The salt of penam derivative (1a) of the invention includes salts of the types known to form with basic groups such as amino or with acidic groups such as hydroxy and carboxy. The salts forming with basic groups include, among others, salts with mineral acids such as hydrochloric acid, sulfuric acid, etc.; salts with carboxylic acids such as formic acid, citric acid, trichloroacetic acid, trifluoroacetic acid, etc.; salts with sulfonic acids such as methanesulfonic acid, benzenesulfonic acid, p-toluenesulfonic acid, mesithyl-enesulfonic acid, naphthalenesulfonic acid and so on. The salts forming with acidic groups include, among others, salts with alkali metals such as sodium, potassium, etc.; salts with alkaline earth metals such as calcium, magnesium, etc.; ammonium salts, and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, N,N'-dibenzylethylenediamine and so on.

Where any species of compound (1a) and salts thereof may occur as isomers (e.g. optical geometrical and tautomeric isomers), all of such isomers as well as all crystalline forms and hydrates are subsumed in the compound of the invention.

The penam derivative (1a) provided in accordance with the invention is an important synthetic intermediate which can be derivatized to other valuable penam compounds by utilizing any, or an appropriate combination, of the hitherto-known reactions such as esterification, hydrolysis, addition, acylation, oxidation, reduction, cyclization, halogenation, alkylation, amination, thiolation, quaternization, aryloxylation, alkylamination, Wittig reaction and so on.

This compound (1a) or salt thereof can be converted to a compound of general formula (1a) wherein $R^1$ is amino by eliminating the acyl group or the amino-protecting group from the protected amino group $R^1$ by any of the processes well known to chemists in this field, such as the processes described in J. Chem. Soc. 83, 320 (1903) or in the specifications of Japanese Patent Publication 49-40479 and 45–40899 or any other process analogous thereto.

Furthermore, this compound of general formula (1a) wherein $R^1$ is an amino group or a reactive derivative of this amino group can be acylated with a carboxylic acid corresponding to any of the acyl groups mentioned for $R^1$ or a reactive derivative of the carboxyl group of such carboxylic acid by any of the processes described in Japanese Unexamined Patent Application 59-9308, 62-135477 and 63-115888 or any process analogous thereto.

The reactive derivative of the amino group of the compound (1a) in which $R^1$ is amino includes, among others, silyl derivatives which can be obtained by reaction with bis(trimethylsilyl)acetamide, trimethyl-silylacetamide, etc.; the corresponding isocyanate and isothiocyanate, and Schiff bases which can be obtained by reaction with aldehydes, e.g. acetaldehyde, benzaldehyde, etc., or ketones, e.g. acetone, methyl ethyl ketone, etc., as well as the corresponding enamine compounds.

The reactive derivative of the carboxyl group of the carboxylic acid corresponding to any acyl group mentioned hereinbefore in connection with $R_1$ includes, among others, acid halides such as acid chloride, acid bromide; mixed acid anhydrides with other acids such as substituted phosphoric acids, dialkylphosphorous acids, sulfurous acid, thiosulfuric acid, sulfuric acid, alkylcarbonic acids, organic carboxylic acids, etc.; active acid amides obtainable with imidazole, dimethyl-pyrazole, etc.; active thioesters with tiols such as benzenethiol, 2-benzothiazolylthiol, etc.; and active esters with N-hydroxy compounds such as N-hydroxypiperidine, N-hydroxysuccinimide,. N-hydroxyphthalimide, etc. or with substituted phenols such as p-nitrophenol.

The compound (1a) in which $R^3$ is a carboxy-protecting group can be converted to a compound (1a) in which $R^3$ is a hydrogen atom by the various carboxy-deprotecting processes described in the aforementioned literature, Chapter 5, pp 152–192 and the specifications of Japanese Unexamined Patent Application No. 50-17991, No. 52-106891 and No. 61-263984, among others.

The compound (1a) of the invention has high antibacterial activity and is of value as a prophylactic and therapeutic agent for bacterial infections.

To administer the compound (1a) or salt of the invention for the therapy or prevention of such diseases, it is generally formulated into suitable pharmaceutical compositions using such known pharmaceutically acceptable carriers, e.g. organic or inorganic excipients which may be solid or liquid, as are fit for oral, parenteral or topical administration. Such preparations may take various dosage forms, solid and liquid, such as tablets, granules, powders, capsules, solutions, suspensions, syrups, emulsions, lemonades and so on. Where necessary, there may be incorporated in such pharmaceutical compositions a variety of adjuvants, stabilizers, lubricants and other common additives such as lactose, magnesium stearate, kaolin, sucrose, corn starch, talc, stearic acid, gelatin, agar, pectin, peanut oil, olive oil, theobroma oil, ethylene glycol and so on.

The dosage of compound (1a) is dependent on the patient's age and condition, diagnosis, species of compound (1a) and other factors. Generally, however, the patient may be given about 1 mg to about 4000 mg, or even more, per day. For the treatment of diseases caused by pathogenic bacteria, the mean unit dosage of compound (1a) may be about 50 mg, 100 mg, 250 mg, 500 mg, 1000 mg or 2000 mg.

EXAMPLES

The following examples are further illustrative of the invention.

Reference Example 1

In 10 ml of N,N-dimethylformamide is dissolved 1 g of the compound of general formula (6) wherein $R^1$=phenylacetamido, $R^2$=hydrogen, $R^3$=diphenylmethyl, X=phenylsulfenyl and $R^5$=trifluoromethyl [hereinafter referred to as compound (6a)]. After the solution is cooled to −30° C., 0.43 ml of triethylamine is added and the reaction is conducted at −30° C. with stirring for 1 hour. The reaction mixture is then extracted with ethyl acetate and the extract is washed with water and dried over anhydrous sodium sulfate. The dry extract is then concentrated under reduced pressure to give a compound of general formula (5) wherein $R^1$=phenylacetamido, $R^2$=hydrogen, $R^3$=diphenylmethyl, and X=phenylsulfenyl [hereinafter referred to as compound (5a)] in a yield of 99%.
NMR CDCl$_3$): δ ppm;

3.61 (s, 2H), 5.31 (dd, 1H, J=5 Hz and 7 Hz), 5.57 and 5.70 (ABq, 2H, J=15 Hz) , 5.84 (d, 1H, J=5 Hz), 6.02 (d, 1H, J=7 Hz), 6.81 (s, 1H), 7.22–7.73 (m, 20H)

Reference Examples 2–7

Using the starting compounds indicated in Table 1, the reaction procedure of Reference Example 1 is otherwise followed to give the following compounds.

TABLE 1

| Reference Example | Compound (6) R¹ | R² | R³ | X | R⁸ | Yield of compound (5) | |
|---|---|---|---|---|---|---|---|
| 2 | PhCH₂CONH | H | CH₂–⟨C₆H₄⟩–OCH₃ | SO₂Ph | CF₃ | 5b | 99% |
| 3 | " | " | " | " | CH₃ | 5b | 86% |
| 4 | " | " | CH₃ | " | CF₃ | 5c | 100% |
| 5 | " | " | CHPh₂ | " | –⟨C₆H₄⟩–CH₃ | 5a | 100% |
| 6 | " | " | " | " | S–(benzothiazol-2-yl-S) | CF₃ | 5d | 99% |
| 7 | H | H | CH₂–⟨C₆H₄⟩–OCH₃ | SO₂Ph | " | 5e | 99% |

Ph: Phenyl

The following is a list of NMR data.
NMR (CDCl₃): δ ppm;

Compound (5b): 3.58 (s, 2H), 3.80 (s, 3H), 5.10 (s, 2H), 5.32 (dd, 1H, J=5 Hz and 8 Hz), 5.60 and 5.47 (ABq, 2H, J=15 Hz), 5.87 (d, 1H, J=5 Hz), 6.08 (d, 1H, J=8 Hz), 6.85–7.83 (m, 14H)

Compound (5c): 3.59 (s, 2H), 3.74 (s, 3H), 5.33 (dd, 1H, J=5 Hz and 8 Hz), 5.54 and 5.64 (ABq, 2H, J=15 Hz), 5.88 (d, 1H, J=5 Hz), 6.02 (d, 1H, J=8 Hz), 7.20–7.90 (m, 10H)

Compound (5d): 3.67 (s, 2H), 5.25 (dd, 1H, J=5 Hz and 8 Hz), 5.69 (d, 1H, J=5 Hz), 5.60 and 5.76 (ABq, 2H, J=15 Hz), 6.71 (s, 1H), 7.00–7.34 (m, 20H)

Compound (5e): 3.02 (dd, 1H, J=2.6 Hz and 15.7 Hz), 3.58 (dd, 1H, J=5.4 Hz and 15.7 Hz), 3.79 (s, 3H), 5.17 (s, 2H), 5.47 and 5.60 (ABq, 2H, J=15.2 Hz), 5.62 (dd, 1H, J=2.6 Hz and 5.4 Hz), 6.87–7.89 (m, 9H)

Reference Examples 8–10

The reaction procedure of Reference Example 1 is repeated except that the reaction solvent and the reaction temperature are altered to give compound (5a) in the yields shown in Table 2.

TABLE 2

| Reference Example | Reaction solvent | Temperature | Yield |
|---|---|---|---|
| 8 | Tetrahydrofuran | –20° C. | 99% |
| 9 | " | 20° C. | 98% |
| 10 | Methylene chloride | –20° C. | 95% |

Reference Example 11

In 1 ml of N,N-dimethylformamide is dissolved 100 mg of the compound of general formula (5) wherein R¹=phenylacetamido, R²=hydrogen, R³=diphenylmethyl and X=phenylsulfenyl [compound (5b)]. To this solution is added 50 mg of zinc dust, followed by addition of 50 mg of BiCl₃. The reaction is conducted at room temperature with stirring for 30 minutes. To this is added 1N-hydro-chloric acid and the mixture is extracted with ethyl acetate. The organic layer is separated, washed with water, dried over anhydrous magnesium sulfate and concentrated under reduced pressure. The residue is purified by silica gel column chromatography to give a compound of general formula (2) wherein R¹=phenylacetamido, R²=hydrogen and R³=p-methoxybenzyl [compound (2b)] in a yield of 92%.

NMR (CDCl₃): δ ppm; 3.61 (ABq, 2H, J=16 Hz), 3.80 (s, 3H), 5.11 (s, 2H), 5.18 (t, 1H, J=1 Hz), 5.24 (t, 1H, J=1 Hz), 5.35 (t, 1H, J=1 Hz), 5.57 (d, 1H, J=4 Hz), 5.75 (dd, 1H, J=4 Hz and 9 Hz), 6.07 (d, 1H, J=9 Hz), 6.85–7.40 (m, 9H)

Reference Example 12

Using 200 mg of compound (5a), the reaction procedure of Reference Example 11 is repeated to give a compound of general formula (2) wherein R¹=phenylacetamido, R²=hydrogen, R³=diphenylmethyl [compound (2a)] in a yield of 89%.

NMR (CDCl₃): δ ppm; 3.62 (s, 2H), 5.26–5.28 (m, 2H), 5.37 (t, 1H, J=2 Hz), 5.61 (d, 1H, J=4 Hz), 5.76 (dd, 1H, J=4 Hz and 9 Hz), 6.14 (d, 1H, J=9 Hz), 6.82 (s, 1H), 7.20–7.41 (m, 15H)

Reference Example 13

In 0.5 ml of N,N-dimethylformamide is dissolved 50 mg of a compound of general formula (5) wherein R¹=phenylacetamido, R²=hydrogen, R³=methyl and X=phenylsulfenyl [compound (5c)]. To this solution are added 50 mg of zinc dust and 10 αl of TiCl₄ and the mixture is stirred at room temperature for 25 minutes. This reaction mixture is after-treated in the same manner as in Reference Example 11 to give a compound of general formula (2) wherein $R^1$=phenylacetamido, $R^2$=hydrogen and $R^3$=methyl [compound (2c)] in a yield of 95%.

NMR CDCl$_3$): δ ppm; 3.62 (ABq, 2H, J=16 Hz), 3.78 (s, 3H), 5.19 (t, 1H, J=2 Hz), 5.28 (t, 1H, J=2 Hz), 5.40 (t, 1H, J=2 Hz), 5.60 (d, 1H, J=4 Hz), 5.77 (dd, 1H, J=4 Hz and 9 Hz), 6.20 (d, 1H, J=9 Hz), 7.27–7.39 (m, 5H)

Reference Example 14

Using 189 mg of the compound of general formula (5) wherein $R^1$=$R^2$=hydrogen, $R^3$=p-methoxybenzyl and X=phenylsulfenyl [compound (5d)], the reaction procedure of Reference Example 11 is repeated to give a compound of general formula (2) wherein $R^1$=$R^2$=hydrogen and $R^3$=p-methoxybenzyl [compound (2d)] in a yield of 88%.

NMR CDCl$_3$): δ ppm; 3.16 (dd, 1H, J=1.5 Hz and 16 Hz), 3.66 (dd, 1H, J=4 Hz and 16 Hz), 3.82 (s, 3H), 5.13 (s, 2H), 5.24 (dd, 1H, J=1.8 Hz and 1.8 Hz), 5.28 (dd, 1H, J=1.8 Hz and 1.8 Hz), 5.32 (dd, 1H, J=1.8 Hz and 1.8 Hz), 5.38 (dd, 1H, J=1.5 Hz and 4 Hz), 6.87–7.30 (m, 4H)

Reference Examples 15–20

The reaction procedure of Reference Example 11 is repeated except that different metals and metal salts are employed to give compound (2b). The results are shown in Table 3.

TABLE 3

| Reference Example | Metal salt | Metal | Time (minutes) | Yield Compound (2b) |
|---|---|---|---|---|
| 15 | PbBr$_2$ | Al | 14 | 89% |
| 16 | GaCl$_3$ | Zn | 30 | 70% |
| 17 | SbCl$_3$ | Zn | 30 | 72% |
| 18 | ZrCl$_4$ | Zn | 60 | 82% |
| 19 | TeCl$_4$ | Zn | 60 | 83% |
| 20 | TiCl$_4$ | Zn | 30 | 85% |

Example 1

In 3 ml of methylene chloride is dissolved 50 mg of compound (2b). To this solution is added 30 mg of m-chloroperbenzoic acid with ice-cooling and the mixture is stirred for 30 minutes. The reaction mixture is then washed with a saturated aqueous solution of sodium hydrogen carbonate and a saturated aqueous solution of sodium chloride in that order, dried over anhydrous sodium sulfate and concentrated under reduced pressure. The residue is purified by silica gel column chromatography to give a compound of general formula (1b) wherein $R^1$ =phenylacetamido, $R^2$=hydrogen, $R^3$=p) methoxybenzyl and m=1 [compound (1b-a)] in a yield of 90%.

NMR CDCl$_3$: δ ppm; 3.60 (s, 2H), 3.81 (s, 3H), 4.80 (d, H, J=4.4 Hz), 4.11 and 5.24 (ABq, 2H, J=11.7 Hz), 5.44 (dd, 1H, J=2.4 Hz and 2.4 Hz ), 5.91 ( dd, 1H, J=2.4 Hz and 2.4 Hz), 6.15 (dd, 1H, J=4.4 Hz and 10.4 Hz), 6.19 (dd, 1H, J=2.4 Hz and 2.4 Hz), 7.11 (d, 1H, J=10.4 Hz), 6.85–6.93 (m, 2H), 7.22–7.40 (m, 7H)

Example 2

In 3 ml of methylene chloride is dissolved 51.4 mg of compound (2b). To this solution is added 126 mg of m-chloroperbenzoic acid and the reaction is conducted at room temperature with stirring for 6 hours. The reaction mixture is then after-treated as in Example 1 to give a compound of general formula (1b) wherein $R^1$=phenylacetamido, $R^2$=hydrogen, $R^3$=p-methoxybenzyl, and m=2 [compound (1b—b)] in a yield of 90%.

NMR (CDCl$_3$): δ ppm; 3.66 (s, 2H), 3.82 (s, 3H), 4.60 (d, 1H, J=4.4 Hz), 5.11 and 5.25 (ABq, 2H, J=11.7 Hz), 5.26 (dd, 1H, J=2.6 Hz and 2.6 Hz), 5.97 (dd, 1H, J=2.6 Hz and 2.6 Hz), 6.14 (dd, 1H, J=2.6 Hz and 2.6 Hz) 6.17 (dd, 1H, J=4.4 Hz and 10.7 Hz), 6.97 (d, 1H, J=10.7 Hz), 6.86–6.93 (m, 2H), 7.23–7.40 (m, 7H)

Example 3

In 1 ml of methylene chloride is dissolved 30 mg of the compound of general formula (2) wherein $R^1$=phenylacetamido, $R^2$=hydrogen and $R^3$=diphenylmethyl [compound (2a)]. To this solution is added 15 mg of m-chloroperbenzoic acid with ice-cooling and the reaction is conducted under stirring for 20 minutes. The reaction mixture is then washed with a saturated aqueous solution of sodium hydrogen carbonate, an aqueous solution of sodium thiosulfate and a saturated aqueous solution of sodium chloride, dried over anhydrous sodium sulfate and concentrated under reduced pressure. The residue is purified by silica gel column chromatography to give a compound of general formula (1b) wherein $R^1$=phenylacetamido, $R^2$=hydrogen, $R^3$=diphenylmethyl and m=1 [compound (1b-c)] in a yield of 92%.

NMR CDCl$_3$): δ ppm; 3.60 and 3.61 (ABq, 2H, J=16 Hz), 4.82 (d, 1H, J=4 Hz), 5.35 (t, 1H, J=2.5 Hz), 5.80 (t, 1H, J=2.5 Hz), 6.14 (t, 1H, J=2.5 Hz), 6.18 (dd, 1H, J=4 Hz and 10 Hz), 6.95 (s, 1H), 7.13 (d, 1H, J=10 Hz), 7.02–7.40 (m, 15H)

Example 4

In 6 ml of methylene chloride is dissolved 85 mg of compound (2d). To this solution is added 300 mg of m-chloroperbenzoic acid and the reaction is conducted at room temperature with stirring for 2 hours. The reaction mixture is then treated as in Example 1 to give a compound of general formula (1b) wherein $R^1$=$R^2$=hydrogen, $R^3$=p-methoxybenzyl and m=2 [compound (1b-d)] in a yield of 78%.

NMR (CDCl$_3$): δ ppm; 3.49 (dd, 1H, J=2.3 Hz and 15.9 Hz), 3.58 (dd, 1H, J=3.6 Hz and 15.9 Hz), 3.83 (s, 3H), 4.52 (dd, 1H, J=2.3 Hz and 3.6 Hz), 5.13 and 5.26 (ABq, 2H, J=11.6 Hz), 5.25 (dd, 1H, J=2.7 Hz and 2.7 Hz), 6.02 (dd, 1H, J=2.7 Hz and 2.7 Hz), 6.23 (dd, 1H, J=2.7 Hz and 2.7 Hz), 6.89–7.33 (m, 4H)

Example 5

First, 0.6 mg (content 60%) of sodium hydride is weighed into a reaction vessel and dried under reduced pressure. To this are added 1 ml of tetrahydrofuran and 15.2 mg of methyl 3-mercaptopropionate and the mixture is stirred at room temperature for 30 minutes. The reaction vessel is then immersed in a dry ice-acetone bath for cooling and a solution of 30 mg of compound (1b-a) in 1 ml of tetrahydrofuran is added. The reaction is conducted at −50° C. with stirring for 1 hour. The reaction mixture is extracted with ethyl acetate and the extract is washed with a saturated aqueous solution of sodium chloride and dried over anhydrous sodium sulfate. The solvent is then distilled off under reduced pressure and the residue is purified by column chromatography to give a compound of general formula (1a) wherein $R^1$=phenylacetamido, $R^2$=hydrogen, $R^3$=p-methoxybenzyl, Y=2-methoxycarbonylethylthio and n=1 [compound (1a-a)] in a yield of 95%.
IR (CHCl₃): 1798, 1738, 1682, 1613, 1518, 1439 cm⁻¹

Example 6

The procedure of Example 5 is repeated except that the compound of general formula (3) wherein Y=allylthio is used in lieu of methyl 3-mercaptopropionate to give a compound of general formula (1a) wherein R¹=phenylacetamido, R²=hydrogen, R³=p-methoxybenzyl, Y=allylthio and n=1 [compound (1a-b)] in a yield of 85%.
IR (CHCl₃): 1800, 1744, 1684, 1613, 1516 cm⁻¹

Example 7

The procedure of Example 5 is repeated except that compound of general formula (3) wherein Y=2-hydroxyethylthio is used in lieu of methyl 3-mercaptopropionate to give a compound of general formula (1a) wherein R¹=phenylacetamido, R²=hydrogen, R³=p-methoxybenzyl, Y=2-hydroxyethylthio and n=1 [compound (1a-c)] in a yield of 91%. IR (CHCl₃): 3382, 2964, 1796, 1744, 1682, 1613, 1518 cm⁻¹

Example 8

The procedure of Example 5 is repeated except that the compound of general formula (3) wherein Y=(CH₃CONH)(CH₃COO)CHCH₂S— ((2-acetamido-2-methoxycarbonyl)ethylthio] is used in lieu of methyl 3-mercaptopropionate to give a compound of general formula (1a) wherein R¹=phenylacetamido, R²=hydrogen, R³=p-methoxybenzyl, Y=(2-acetamido-2-methoxycarbonyl)ethylthio and n=1 [compound (1a-d)] in a yield of 95%.
IR (CHCl₃): 2960, 1798, 1744, 1676, 1615, 1586, 1518 cm⁻¹

Example 9

The procedure of Example 5 is repeated except that the compound of general formula (3) wherein Y=2-methoxycarbonylethylthio is used in lieu of methyl 3-mercaptopropionate to give a compound of general formula (1a) wherein R¹=phenylacetamido, R²=hydrogen, R³=p-methoxybenzyl, Y=2-methoxycarbonylethylthio and n=1 [compound (1a-e)] in a yield of 76%.
IR (CHCl₃): 2936, 1794, 1744, 1667, 1615, 1586, 1518 cm⁻¹

Example 10

The procedure of Example 5 is repeated except that the compound of general formula (3) wherein Y=2-furyl-methylthio is used in lieu of methyl 3-mercaptopropionate to give a compound of general formula (1a) wherein R¹=phenylacetamido, R²=hydrogen, R³=p-methoxybenzyl, Y=2-furylmethylthio, and n=1 [compound (1a-f)] in a yield of 59%. IR (CHCl₃): 2938, 1792, 1734, 1661, 1615, 1589, 1495 cm⁻¹

Example 11

In 2 ml of N,N-dimethylformamide is dissolved 36.2 mg of compound (1a-a) and the solution is cooled to −30° C. To this solution is added 12 αl of phosphorus tribromide and the reaction is carried out at −30° C. with stirring for 1 hour. The reaction mixture is then extracted with ethyl acetate and the extract is washed with a saturated aqueous solution of sodium chloride and dried over anhydrous sodium sulfate. The solvent is then distilled off and the residue is purified by column chromatography to a give compound of general formula (1a) wherein R¹=phenylacetamido, R²=hydrogen, R³=p-methoxybenzyl, Y=2-methoxycarbonylethylthio and n=0 [compound (1a-g)] in a yield of 85%. IR (neat): 1785, 1734, 1669, 1615, 1586, 1518, 1456, 1439 cm⁻¹

Example 12

Using compound (1a-b), the procedure of Example 11 is otherwise repeated to give a compound of general formula (1a) wherein R¹=phenylacetamido, R²=hydrogen, R³=P-methoxybenzyl, Y=allylthio and n=0 [compound (1a-h)]in a yield of 74%.
IR (neat): 1787, 1744, 1667, 1613, 1586, 1518, 1456 cm⁻¹

Example 13

To 1 ml of phenol fused at 45° C. is added 13 mg of compound (1a-g) followed by addition of 2 αl of 35% hydrochloric acid. The reaction is conducted at the same temperature with stirring for 2 hours. The reaction mixture is then diluted with ethyl acetate and extracted with a 5% aqueous solution of potassium hydrogen carbonate. The aqueous extract is neutralized with 5% hydrochloric acid and passed through a Sephadex LH-20 column. The fractions containing the desired product are pooled and lyophilized to give a compound of general formula (1a) wherein R¹=phenylacetamido, R²=hydrogen, R³=K, Y=2-methoxycarbonylethylthio and n=0 [compound (1a-i)]. IR (KBr): 1782, 1740, 1672, 1624 cm⁻¹

Antibacterial Activity Assay

Using compound (1a-i), an in vitro antibacterial potency test was performed by the doubling dilution agar plate method. Each test strain was cultured in a sensitivity assay bouillon for 20 hours and 0.005 ml of the culture (viable cell count: ca. 10⁸ /ml) was inoculated on a sensitivity assay agar medium containing a varying concentration of the antibacterial compound.
After 20 hours of incubation at 37° C., the minimal inhibitory concentration (MIC) was determined and expressed in units of μg/ml. The results are shown in Table 4.

TABLE 4

| Test organism | MIC |
|---|---|
| Staphylococcus aureus 209P | 0.1 |
| Staphylococcus aureus, methicillin-resistant | 100 |
| Escherichia coli NIHJ-JC2 | 12.5 |
| Proteus vulgaris | 0.39 |
| Serratia marcescens | 12.5 |
| Pseudomonas aeruginosa | 100 |

What is claimed is:
1. A penam compound of the formula

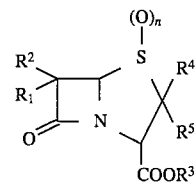

wherein R¹ means hydrogen, halogen, amino or protected amino; R² means hydrogen, halogen, lower alkoxy, lower acyl, lower alkyl, hydroxy-substituted lower alkyl, protected hydroxy-substituted lower alkyl, hydroxy or protected hydroxy; or R¹ and R² may jointly represent oxo; R³ means hydrogen or a carboxy-protecting group; R⁴ means hydrogen; $R^5$ means a group of the formula —$CH_2Y$ where Y means allylthio or —$SR^6$; $R^6$ means a lower alkyl group, or which group is unsubstituted or substituted by a substituent selected from the group consisting of halogen, hydroxy, nitro, cyano, phenyl, naphthyl, lower alkyl, amino, mono-lower alkylamino, di-lower alkylamino, mercapto, alkylthio, phenylthio, naphthylthio, formyloxy, lower alkanoyloxy, benzoyloxy, naphthyloyloxy, formyl, lower alkanoyl, benzoyl, naphthyloyl, lower alkoxy, phenoxy, naphthyloxy, carboxy, lower alkoxy carbonyl, phenoxy carbonyl and naphthyloxy carbonyl; and n means 0, 1 or 2.

2. The compound according to claim 1, wherein $R^4$ means hydrogen and Y means allylthio.

3. The compound according to claim 1, wherein n is equal to 1 or 2.

* * * * *